United States Patent [19]
Colon et al.

[11] Patent Number: 5,991,731
[45] Date of Patent: Nov. 23, 1999

[54] METHOD AND SYSTEM FOR INTERACTIVE PRESCRIPTION AND DISTRIBUTION OF PRESCRIPTIONS IN CONDUCTING CLINICAL STUDIES

[75] Inventors: Michael Colon; Ronald G. Marks; Carl J. Pepine; Eileen M. Handberg-Thurmond; Rhonda M. Cooper-DeHoff; Phillip Padgett, all of Gainesville, Fla.

[73] Assignee: University of Florida, Gainesville, Fla.

[21] Appl. No.: 09/241,140

[22] Filed: Feb. 1, 1999

Related U.S. Application Data

[63] Continuation of application No. 08/811,446, Mar. 3, 1997, abandoned.

[51] Int. Cl.$^6$ .................................................. G08B 5/22
[52] U.S. Cl. .................................................. 705/3; 705/2
[58] Field of Search ........................ 705/2, 3, 10, 14

[56] References Cited

U.S. PATENT DOCUMENTS

| | | | |
|---|---|---|---|
| 5,319,543 | 6/1994 | Wilhelm | 705/3 |
| 5,572,421 | 11/1996 | Altman et al. | 705/3 |
| 5,597,995 | 1/1997 | Williams et al. | 235/375 |
| 5,666,490 | 9/1997 | Gillings et al. | 395/200.68 |
| 5,713,350 | 2/1998 | Yokota et al. | 600/300 |
| 5,737,539 | 4/1998 | Edelson et al. | 705/3 |
| 5,822,544 | 10/1998 | Chaco et al. | 395/202 |

FOREIGN PATENT DOCUMENTS

| | | | |
|---|---|---|---|
| WO 96/13790 | 5/1996 | WIPO | G06F 159/00 |

OTHER PUBLICATIONS

Kelly, M.A. and Oldham, J.; The Internet and Randomized Controlled Trials, European Congress of the Internet in Medicine, MEDNET 96, http://www.mednet.org.uk/mednet/mednet96.htm, Oct. 1996.

Carpenter, Rebecca, Canadian Business, Drugnet on Trial, vol. 69, Is:8, p.33, Jul. 1996.

Winslow, Ron, Technology (a Special Report) Desktop Doctors: Medical Technology Isn't Always about surgery and diagnosis, get ready for the paperless doctor's office, The Wall Street Journal, Sec. R, p. 14, Apr. 6, 1992.

Valeriano, Lourdes Lee, Business Bulletin: A Special Background Report on Trends in Industry and Finance, The Wall Street Journal, Sec: A p. 1, Nov. 1992.

Gillespie M.J. et al, Distributed Data Entry in a Collaborateive Medical Study (CASS): Seven Years Experience, Proceedings of Computer Networks COMPCON 82. Twenty Fifth IEEE Computer Society International Conference, Washington, DC, Sep. 20–23, 1982.

King C et al, MEDUS/A: Distributing Database management for Medical ResearchProceedings of Computer Netoworks COMPCON 82. Twenty Fifth IEEE Computer Society International Conference, Washington, DC, Sep. 20–23, 1982.

(List continued on next page.)

*Primary Examiner*—Allen R. MacDonald
*Assistant Examiner*—Jagoish Patel
*Attorney, Agent, or Firm*—Quarles & Brady LLP

[57] ABSTRACT

A computer system (11, 12, 13) and method for managing data used in conducting clinical studies concerning subjects at a plurality of participating, geographically distributed clinical sites, each participating clinical site having a computer (17, 18, 19) for inputting, transmitting and receiving data over the Internet (15). An Internet network server computer (13) is interfaced to a database host computer (11) through a private network (12). The system (11, 12, 17, 18, 19) communicates data over the Internet (15, 16) to determine patient eligibility, randomization and initial prescriptions, which can then be adjusted by the physician online. The final prescription is printed out for signature and sent electronically to a distribution center (55). Study data is maintained in a database in the host computer (11) behind a firewall provided in the Internet server computer (13).

20 Claims, 5 Drawing Sheets

OTHER PUBLICATIONS

Kelly M.A. et al, The Internet and Randomized Controlled Trials, Internet in Medicine. MEDNET 96, Brighton, UK 1996, V. 47, No. 1–2, ISSN 1386–5056, Nov. 1997.

Piffero V et al, Computerization of a Clinical trial to acquire data in real–time and to manage them with a network of laptop computers using user–friendly Software, MEDINFO 89. Proceedings of the Sixth Conference on Medical Informatics, Beijing, China an, Oct. 1989.

METHOD AND SYSTEM FOR INTERACTIVE PRESCRIPTION AND DISTRIBUTION OF PRESCRIPTIONS IN CONDUCTING CLINICAL STUDIES

CROSS-REFERENCE TO RELATED APPLICATION

This is a continuation of U.S. patent application Ser. No. 08/811,446 filed Mar. 3, 1997, and now abandoned.

TECHNICAL FIELD

The invention relates to methods and systems for interactive prescription and distribution of prescriptions over the Internet, and more particularly, in the context of clinical studies conducted with large numbers of clinical study investigators and study participants.

DESCRIPTION OF THE BACKGROUND ART

Prior networked systems for transferring clinical study information from remote sites typically used personal computers or work stations operating with a specific Windows or Macintosh or UNIX operating system and using various communications software programs to communicate through telephone lines from remote sites. This required updating software individually at each site as upgrades or other changes were needed, and the data was typically communicated in unencrypted form.

Prior known systems for managing the distribution of prescriptions have been located at the pharmacy distribution centers, and have not typically had input from clinical study investigators, such as physicians, over the Internet.

SUMMARY OF THE INVENTION

The invention provides an Internet-networked system with online communication to a computing center from a large number of clinical study investigators at numerous and diverse locations remote from the computing center. Internet software is also made available, at offices of the clinical study investigators and this system is interactive between the center and the offices of the clinical study investigators to determine parameters of the prescriptions, for example. The system is particularly useful for large clinical studies of new drugs in determining patient eligibility, randomization and prescriptions online, while the patient is available in a physician's office.

In a detailed particular embodiment, the system handles automatic assignment and randomization of thousands of participants in a clinical study with respect to care strategies to be administered to the study participants. This is a very important aspect of the clinical studies and trials, and is controlled according to scientifically developed mathematical and statistical methods. In the randomization routine, the system of the present invention efficiently makes the assignments in a quick and efficient manner, while still allowing control by the study investigators in the treatment of the study participants. The computer-aided randomization replaces a part of the clinical study that was in some cases performed manually. The invention allows larger studies to be conducted at more diversely distributed locations with lower costs for technical support and computer software at the remote sites.

The system captures data in its database through appropriate input forms developed for the specific clinical study. Data is stored online and reports are produced in real time to study investigators and to the sponsor regarding sites that are participating, recruitment levels by participating site, patient follow-up, and significant events. The database will also provide the sponsor with an online accounting of study funds distribution.

In the eligibility routine, the system determines at the time when patient data is submitted, whether the patient qualifies for the clinical study, and if not, a message is communicated to the clinical study investigator's computer.

The invention improves the distribution of prescribed items to patients as part of the clinical study. Eligible patients are identified immediately and randomized to a care strategy on-line while they are still in the physician's office. As the patient is randomized to a care strategy online, a clinical study investigator has the recommended prescription appear on the computer screen. The investigator may modify it within study parameters, and then submit it electronically to the study management center, which then forwards the prescription to a distribution center. This distribution center provides prescriptions to all participants.

Online data entry is restricted to authorized users only and data transmissions may be encrypted to ensure confidentiality.

The system of the present invention can also be applied to other educational activities in which data is to be acquired, processed and parameters returned to the local sites for further action.

Other objects and advantages of the invention, besides those discussed above, will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and therefore, reference is made to the claims which follow the description for determining the scope of the invention.

DETAILED DESCRIPTION OF THE PREFERRED EMBODIMENT

Figure 1:
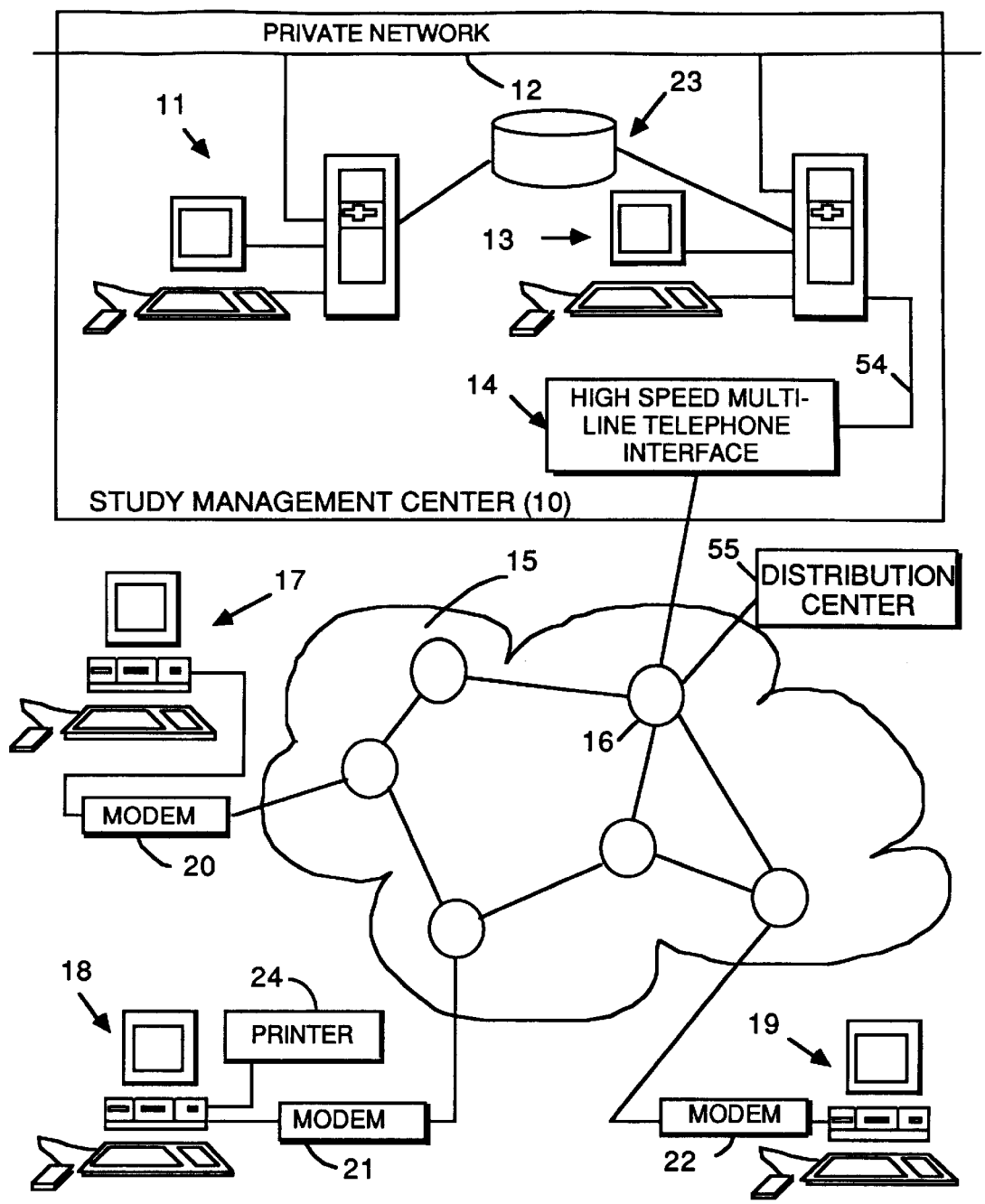
FIG. 1 is schematic circuit diagram of the system of the present invention.

Referring to FIG. 1, the system of the present invention includes a study management center 10, also referred to more generally as a computing center 10, at a particular geographical site. The computing center 10 has a database host computer 11 connected via a 100-Mbit private network 12 to an Internet (Worldwide Web site) server 13. The private network 12 uses known LAN technology, but is not generally accessible to users outside the computing center 10. The Internet server 13 is equipped with two Ethernet adapters (not shown), one of which connects to the private network 12 for communication with the database host computer 11. The Internet server 13 is connected through the other Ethernet adapter to a local area network (LAN) 54, which in turn connects to a high speed multi-line telephone interface 14. This interface 14 connects through the Worldwide Web (Internet) network 15 and its many nodes 16 to computers 17, 18 and 19 at numerous medical offices and facilities throughout the country, and possibly outside the country. These remote computers 17, 18 and 19 typically connect through modems 20, 21 and 22 to the Internet 15. The remote sites may include physician's offices, the offices of the sponsor of the clinical study, and the offices of the clinical study managers and offices of government agencies.

The database host computer 11 is preferably at least a 166-Mhz Pentium-based computer running the Windows NT operating system and database application software. The database application software is preferably the Oracle Relational Database Management System (DBMS), which is used to store study data for eligibility, randomization, follow-up, endpoint and management. Each type of data is stored in a separate table. Tables are joined as needed to produce regional and study-level management summaries and databases for statistical analysis.

The Internet server 13 is preferably a SUN Microsystems Ultrasparc server running the Solaris 2.5 operating system. This server 13 is used to provide Internet network services to all authorized users over the Internet. The server 13 is also preferably loaded with Netscape Enterprise Server software, which is used to respond to all requests. Authorization is done in real-time against a management database stored behind a firewall on a database host computer 11. The Ultrasparc server 13 provides the firewall between outside connections to the Internet and its connection on a private network 12 to the database host computer 11.

The Internet server 13 preferably uses the Netscape Secure Server software with a Verisign Certificate of Authentication to provide encryption of all material moving to and from the central Internet server.

Secure socket layer level 3 security will be performed at the Internet server 13 using RSA 40-bit encryption (international standard). This encryption system is sufficiently difficult to break that it is the international standard for secure commercial activity on the Internet.

JavaScript is used to create a script to implement client-side validation in real-time of data entry attempts. Each field in the online input forms will be checked in real-time for valid values. Only valid values are permitted to pass into the data system.

The computers 17, 18 and 19 at the clinical study participation sites connect to the Internet (Worldwide Web) 15 through local Internet Access Points which exist throughout the geographical regions in which the study is be conducted. Site investigators are provided with Internet access in order to participate. The computers 17, 18 and 19 at the clinical study participation sites are preferably IBM-PC compatible computers running the Windows '95 operating system, however, Apple Macintosh computers, IBM-PC compatible computers running Windows NT, Windows 3.1, and Unix-compatible Computers running Solaris (Sun UNIX), AIX (IBM UNIX), and Linux (public UNIX) can also be used.

The Internet server 13 (Web Site) and database are backed up. A RAID level 5 disk mirroring system 23 is used to provide redundant online swappable disk storage. The system will automatically switch to a mirrored back-up drive with no loss of service. The failed drive can be removed from the system and replaced with a functional drive without having the Internet network server 13 or database host computer experience downtime.

Figure 3:
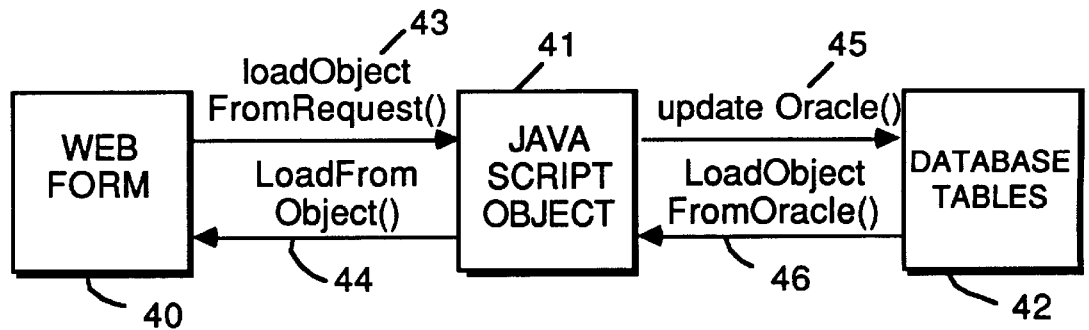
FIG. 3 is a block diagram of a software interface between Internet-network server and the database host computer of FIG. 1.

The Internet Server preferably runs Netscape "Livewire" application software behind the firewall to move data to and from the database on host computer 11. Referring to FIG. 3, a JavaScript object 41 (see example in Appendix A) had been designed to run on the Internet server 13 to mediate the passage of data between the Internet server 13 and the database host computer 11. This object 41 has an element of data for each element of data that is either part of the database tables (represented collectively by element 42 in FIG. 3) or used in one of the Internet database input forms 40 communicated between the Internet server 13 and the remote site computers 17, 18 and 19. Some items may only be found on input forms 40 such as the date (day, month, year), while other items may only be in the database tables 42 (row stamp values, for example). The JavaScript object 41 is used to retrieve values from the database tables 42 and send them to forms viewed on the computers 17, 18 and 19 at the remote sites, and the JavaScript object 41 is also used to retrieve values input to the forms and store them in the database. This script simplifies the programming required to keep track of the types of data elements used in the forms, as well as their disposition, checking and validation. One object 41 is provided for each form 40. Several forms 40 may be used to provide views to tables 42 in the database.

Also shown in FIG. 3 are the functions which are executed to actually transfer data. The function "LoadObject FromRequest()" 43 moves data from the form 40 to the object 41. The function "updateOracle()" 45 moves data from the object 41 to the database tables 42. The function "LoadObject FromOracle()" 46 moves data from the database tables 42 to the object 41. The function "LoadFromObject()" 44 moves data from the object 41 to the form 40.

Figure 2:
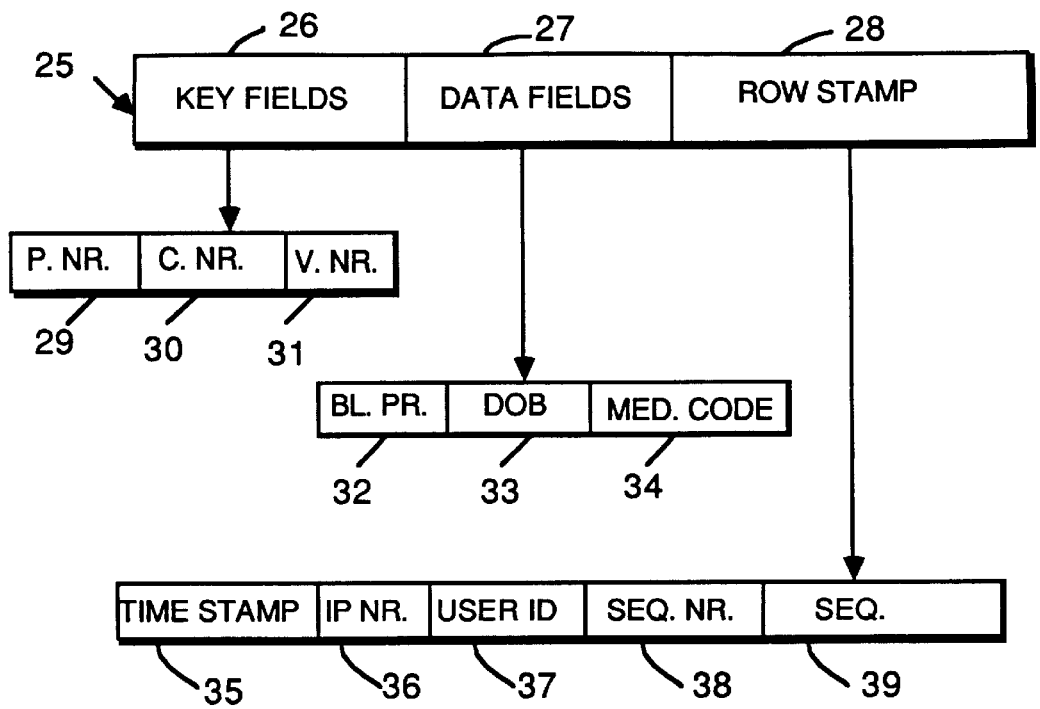
FIG. 2 is a block diagram of a row in the database of the system of FIG. 1.
Figure 4:
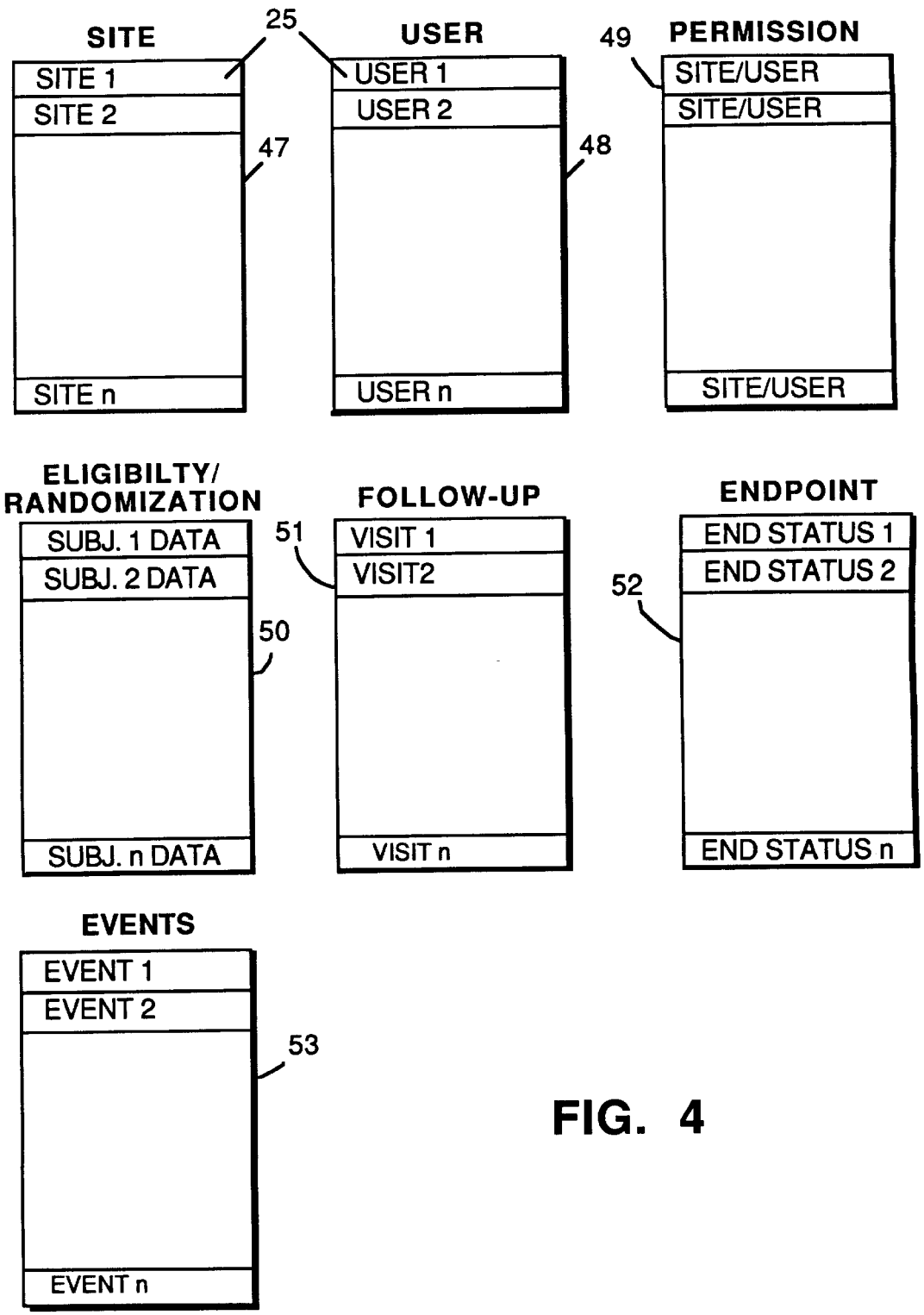
FIG. 4 is a block diagram of certain tables in the database of the system of FIG. 1.

FIG. 2 illustrates the organization of a single row 25 in the database tables 47–53 seen in FIG. 4. Each table 47–53 has rows corresponding to real-world items of interest. Each row has three sections referred as key fields 26, data fields 27 and a row stamp 28.

Key fields 26 provide user-view identifiers for rows. Examples include patient number data 29, center number data 30, and visit number data 31. Users typically use values of key fields to locate and choose rows 25. Key values may or may not be unique in the table. By use of sequences (see below), key field values cannot be edited without damage to the integrity of the database.

Data fields 27 contain the information to be recorded on the row 25. Examples include numeric data such as blood pressure data 32, date fields such as date of birth (DOB) data 33, and binary values such as presence or absence of a particular medical condition 34.

Each row 25 contains a collection of attributes collectively referred to as the row stamp 28 and used to identify and process the record. A time stamp 35 is provided in the form of a date and time (GMT) this record was created. This is followed by an Internet Protocol number 36 of the computer used to create this record. By recording IP numbers 36 the number of computers used to access the database can be determined. A User ID 37 is assigned to each clinical study site. The User ID 37 of the operator is recorded on each record to identify the person making the change. Each record in the table is given a primary sequence number 38, generated consecutively across the lifetime of the table. Each record contains a secondary sequence number 39 to distinguish from the original record from which an edit copy of the record was derived. On original records, the secondary sequence number 39 and the primary sequence number 38 are identical. On edited copies of the row, the secondary sequence numbers 39 will increase with each edit.

Each row 25 corresponds to an instance of the record at a particular moment in time. As the record is changed, new copies of the record are generated. By counting the number of record copies, the number of times the record has been edited can be determined. By ordering records by time stamp 35, a history of all changes to the record can be maintained. By selecting the record whose time stamp 35 is the next closest one before a particular data, the database can be easily rolled back to any point in time.

Referring to FIG. 4, tables 47–53 are provided for each clinical study. The site table 47 contains one row 25 for each site (Site 1, Site 2 . . . Site n) in a study and contains contact information for the remote clinical sites. The user table 48 contains one row 25 for each authorized participating person or office (user) for accessing information and contains contact information related to the user. The permission table 49 contains one row for each site or region the user is authorized to access. Fields in table 49 contain flags (on/off) that are used to authorize a user for access to information about sites, regions and study level information.

The eligibility/randomization table 50 contains one row for each subject enrolled in a study (Subj. 1 Data, Subj. 2 Data . . . Subj. n Data). The clinical study application software in the Internet network server computer 13 includes a randomization routine. Only the randomization software has access to read from and write into randomization files in tables 47 and 50 in the database host computer 11. Eligibility/randomization contains demographics data, eligibility data and the results of the randomization. There is one row 25 for each patient randomized in the study.

The randomization routine assigns study patients to study medications using a random number generator and validated random assignment algorithms. Random numbers are generated using a "C" programming language function that generates a pseudo-random sequence of random numbers with good performance properties. A random number seed controls this sequence. The routine initiates each site with its own seed and maintains the seed following each use for each site. This insures that the sequence of random assignments can be completely reproduced during an audit. The randomization is done using permuted blocks of different sizes. The steps are as follows for each site:

1. A seed is generated using the system clock as a starter seed. The seed is recorded in table 47 in relation to a specific site.
2. Using the seed, a random number is generated. If the number is less than 0.5, a block of a first size is generated, otherwise a block of a second size is generated. The block is recorded in the site records of table 47.
3. When an assignment is to be made, a query is made of the site records. The leading digit in the block is used to assign the patient. If the block is exhausted, a new block is generated as in step 2. The block as depleted or regenerated is stored back in the site records along with the updated seed, if any. The resulting random assignment is stored in table 50.

If connectivity to the database is lost during the process, the randomization can be restarted using the previously sorted checkpoint of seed and block. The entire sequence of assignments can be regenerated using the original seed and following the algorithm for each assignment.

Referring again to FIG. 4, the follow-up table 51 contains one row 25 for each visit by a patient in a study physician. Typical data in each row 25 includes medical measurements taken at the visit and prescription information.

The endpoint table 52 contains one row 25 for each patient in a study. Typical data includes the date of the endpoint and the type of endpoint (death, loss to follow-up, administrative censoring).

The significant events table 53 contains one row 25 for every significant event experienced by a patient in a study. Significant event information includes date of event, severity of event, and action taken. Significant event rows are automatically forwarded via electronic mail to the sponsor and the coordinating centers.

Authorization levels may be provided to restrict access to patient information and functions. Study investigators, sponsors and regional directors have different levels of authorization and access tied to actions and subsets of data. For example, physicians would have authority to enter eligibility data, randomize subjects, enter the follow-up data and review case listings.

Figure 5:
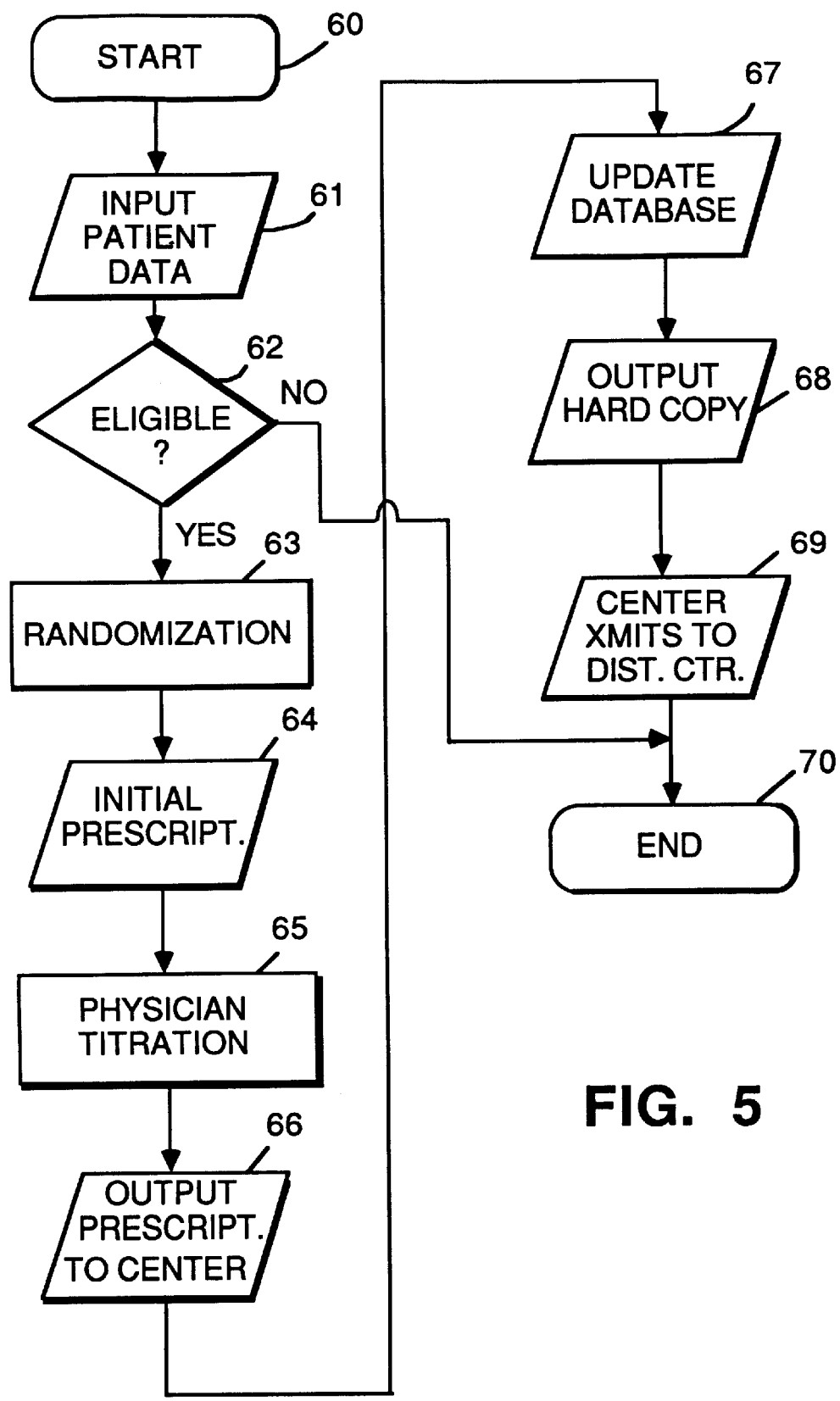
FIG. 5 is a flow chart of the operation of the system of FIG. 1 on a first patient visit.

Referring to FIG. 5, the operation of the computer system will now be described with respect to an initial patient visit. Startup of the clinical study application software at the remote site computers 17, 18 and 19 is represented by the start block 60 in FIG. 5. A form comes up on the screen of one of the computers 17, 18 or 19 and patient data is entered relating to identification, demographics and medical conditions. This information is transmitted to the study management center 10, as represented by input block 61.

Data elements are validated at entry, in real time, ensuring accurate data. Printouts of the same data are included for the patient's permanent record.

Secure transactions are used to pass clinical data over the Internet and conduct clinical study management over the Internet. Security is achieved by restricting access to all Internet material to authorized users only and encrypting data transmissions.

After data is sent to the study management center 10, an application program in the Internet network server computer 13 executes a test to see if the patient meets the eligibility parameters for the study, as represented by decision block 62. If the answer is "NO," as represented by the "NO" branch from block 62, then a message of ineligibility is returned and the procedure is terminated as represented by proceeding to the "END" block 70. If the answer is "YES," as represented by the "YES" branch from block 62, then the patient is randomized based on the data received at the study management center 10, utilizing the randomization routine in the database host computer 11. This is further represented by process block 63 in FIG. 5. The routine assigns the patient to one of the study strategies and stores the results. Based on this determination, the Internet server 13 sends an initial suggested drug prescription to the remote site computer 17, 18 or 19, as represented by output block 64. The attending physician can then confirm or adjust the prescription by entering data to modify data in the drug prescription form. The ability to modify the prescription data is limited by a clinical study protocol, so that prescriptions are not received which are outside the parameters of the study. The procedure to confirm or adjust is referred to as physician titration, and represented by process block 65. The results of the physician's titration are sent to the Internet server computer 13, as represented by output block 66. The results are then transferred to the database host computer 11 and the database is updated, as represented by output block 67. A hard copy of the final drug prescription is printed on a printer at the remote site, such as printer 24 shown in FIG. 1, as represented by output block 68. The physician signs the hard copy to confirm the prescription. The prescription is sent via the Internet network server 13 to a drug distribution center 55 (FIG. 1) for mailing of the prescription to the subject patient, as represented by output block 69. The process is then ended as represented by end block 70.

Figure 6:
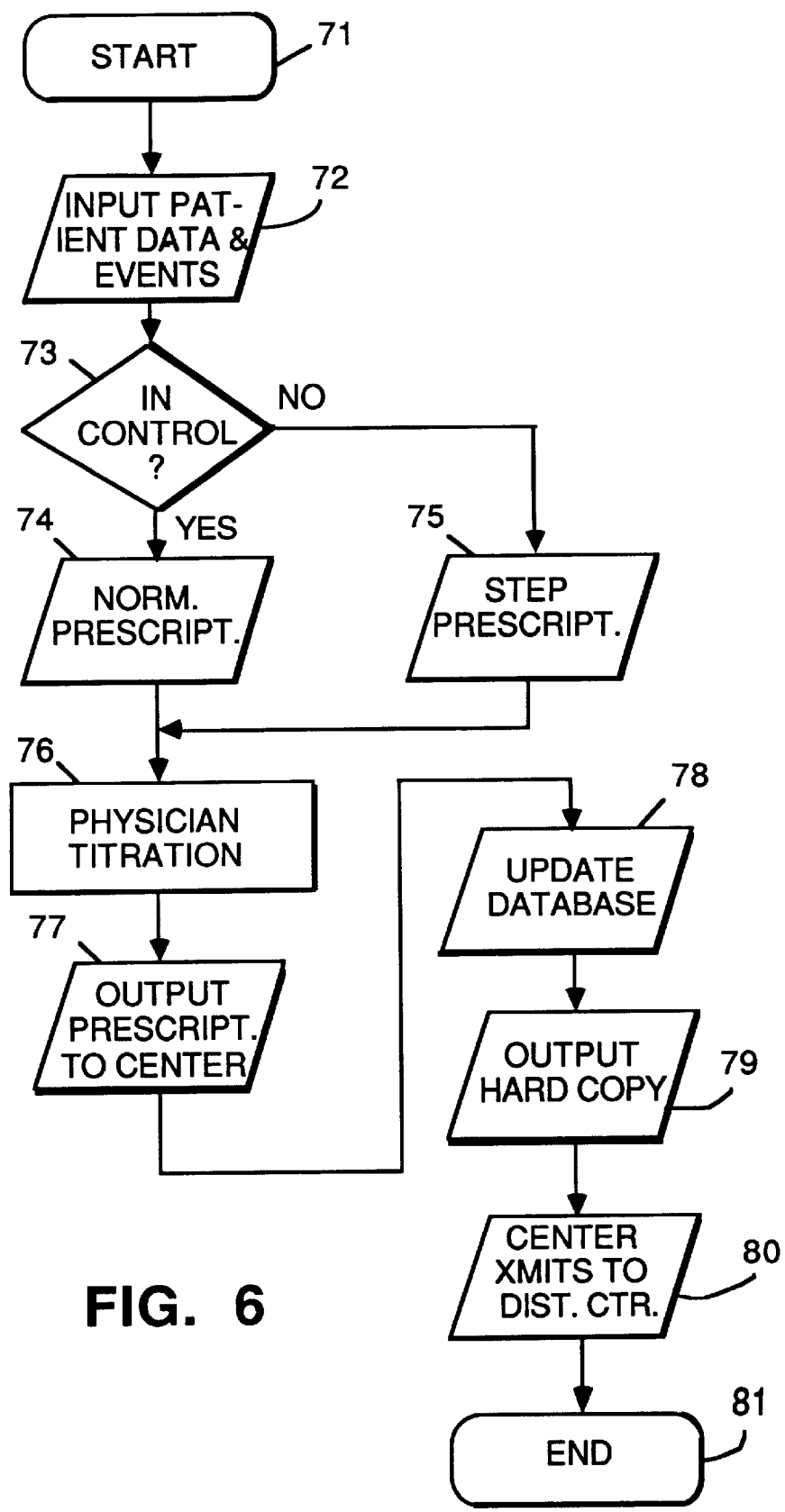
FIG. 6 is a flow chart of the operation of the system of FIG. 1 on subsequent patient visits.

The study will also include follow-up visits and the operation of the system for these consultations with a physician at the participating sites is illustrated in FIG. 6. After starting up and initializing the system, represented by start block 71, follow-up data, end-point data and significant events data is entered, as represented by input block 72, and after verification, is transmitted through the Internet server 13 to the database host computer 11 for input to tables 51, 52 and 53. The application program in the Internet server computer 13 executes a test to see if the patient meets an "in control" parameter for the study, as represented by decision block 73. If the answer is "NO," as represented by the "NO" branch from block 73, then a stepped prescription is transmitted to the physician for consideration and titration, as represented by output block 75. This step represents more aggressive treatment than is the norm for the study. If the answer is "YES," as represented by the "YES" branch from block 73, then a prescription which is normal for the study, possibly the last prescription, is transmitted to the physician for titration, as represented by input/output block 74. The attending physician can then confirm or adjust the prescription by entering data to modify data in the drug prescription form. The ability to modify the prescription data is limited by a clinical study protocol, so that prescriptions are not received which are outside the parameters of the study. The procedure to confirm or adjust is referred to as physician titration, and represented by process block 76. The results of the physician's titration are sent to the Internet server computer 13, as represented by output block 77. The results are then transferred to the database host computer 11 and the database is updated, as represented by output block 78. A hard copy of the final drug prescription is printed on a printer at the remote site, such as printer 24 shown in FIG. 1, as represented by output block 79. The physician signs the hard copy to confirm the prescription. The prescription is sent via the Internet network server 13 to a drug distribution center 55 (FIG. 1) for mailing of the prescription to the subject patient, as represented by output block 80. The process is then ended as represented by end block 81.

An administrative office associated with the central computing facility has to authorize access to the system. The database stores contact information for all study participants and their authorized levels of access. Requests for interaction with the system coming from Internet sites are checked against the management database to assure that only authorized users can access study materials and then only materials appropriate to their role in the study (regional director, study investigator, sponsor representative).

Regional directors, investigators and sponsor representatives for the clinical study are issued passwords for the purpose of conducting study-related activities over the Internet. These passwords are tied to authorized actions and subsets of the data. For example, a site investigator would have the codes to enter eligibility data, randomize subjects, enter follow-up data and review case listings. Regional directors would have access to screens for requesting and obtaining on-line management reports for their respective regions. Study investigators and sponsor representatives would have access to study-wide management reports.

Management data is maintained in the same database as the other study data. This insures consistent operation and access across all activities. Online study management reports are available to authorized users. These reports provide information for monitoring recruitment progress, identification of slow participants, and direct monitoring of follow-up at study, region and site levels.

Statistical Analysis System (SAS) is used to produce data summaries for management reports and statistical analyses. Additional software to be used includes Perl, a powerful scripting language, and S, a system for data analysis and graphics.

This has been a description of a preferred embodiment of the method and apparatus of the present invention. Those of ordinary skill in this art will recognize that modifications might be made while still operating within the spirit and scope of the invention, and to further define the invention, the claims which follow Appendix A are made.

APPENDIX A

Script for Transfer of Data

```
function endpointObject () {
//
// this is server side JavaScript code
//
this.table="invendp"
this.keyname="siid"
this.keyvalue=""
this.location="ok.html"
this.formname="endpoint"
this.elements=new SlotArray(18)
this.elements[1].name="siid"
this.elements[1].type="text"
this.elements[1].value=""
this.elements[1].oracle=true
this.elements[1].changed=true
this.elements[1].form=true
this.elements[1].validate=""
this.elements[1].create="client.siid"
this.elements[1].quote="character"
this.elements[1].key=true
this.elements[1].search=true
this.elements[2].name="ptid"
this.elements[2].type="text"
this.elements[2].value=""
this.elements[2].oracle=true
this.elements[2].changed=true
this.elements[2].form=true
this.elements[2].validate=""
this.elements[2].create="client.ptid"
this.elements[2].quote="character"
this.elements[2].key=true
this.elements[2].search=true
this.elements[3].name="enddate"
this.elements[3].type="text"
this.elements[3].value=""
this.elements[3].oracle=true
this.elements[3].changed=true
this.elements[3].form=false
this.elements[3].validate="new Date (request.year, request.month-1,request.day)"
this.elements[3].create=""
this.elements[3].quote="character"
this.elements[3].key=false
this.elements[3].search=true
this elements[4].name="month"
this elements[4].type="text"
this elements[4].value=""
this elements[4].oracle=false
```

```
this elements[4].changed=false
this elements[4].form=true
this elements[4].validate=""
this elements[4].create="getMonthFromString
    (obj.elements[3].value)"
this elements[4].quote="character"
this elements[4].key=false
this elements[4].search=false
// Code for additional elements removed for illustration
this.elements[17].name="created"
this.elements[17].type="text"
this.elements[17].value=""
this.elements[17].oracle=true
this.elements[17].changed=false
this.elements[17].form=false
this.elements[17].validate=""
this.elements[17].create="new Date()"
this.elements[17].quote="date"
this.elements[17].key=false
this.elements[17].search=false
this.elements[18].name="seq"
this.elements[18].type="text"
this.elements[18].value=""
this.elements[18].oracle=true
this.elements[18].changed=false
this.elements[18]. form=true
this.elements[18].validate=""
this.elements[18].create=""
this.elements[18].quote="character"
this.elements[18].key=false
this.elements[18].search=false
return this
)
```

We claim:

1. A computer system for conducting a clinical study concerning subjects at a plurality of participating sites, each participating site having a computer for inputting, transmitting and receiving data over the Internet, said participating sites being remote from a study management site for managing the clinical study, the computer system comprising:
   a host computer including means for receiving identification, demographic and medical data about the subjects from the participating sites;
   an Internet network server computer including means connected for receiving said identification, demographic and medical data about the subjects from the participating sites over the Internet and means connected for transferring said identification, demographic and medical data about the subjects to said host computer, said Internet network server computer thereafter executing a randomization routine by which the subjects are randomized to respective treatment strategies and responding to such randomization by transmission of a proposed prescription to one of the computers at the participating sites; and
   a participating site communication program for running on computers at the participating sites for inputting, encrypting and transmitting identification, demographic and medical data about the subjects to the study management computer and for receiving from the Internet server computer, and displaying, data comprising said proposed prescription.

2. The computer system of claim 1, wherein the participating site communication means further comprises means for confirming or adjusting the prescription being displayed and means for communicating a confirmed or adjusted prescription to the Internet server computer.

3. The computer system of claim 1, wherein said host computer includes means for receiving said demographic and medical data and means responsive thereto to determine either non-eligibility or eligibility for participation of a subject in the clinical study.

4. The computer system of claim 1, wherein said participating site communication means includes means for transmitting said prescription confirmed or adjusted by the physician to the Internet server computer for transfer to the host computer, and wherein the Internet server computer includes means for transmission of said prescription to a distribution center.

5. The computer system of claim 1, wherein said participating site communication means includes means for printing out a prescription selected by a physician in response to said proposed prescription.

6. The computer system of claim 1, wherein the host computer including means for receiving identification, demographic and medical data about the subjects from the participating sites further includes a relational database.

7. The computer system of claim 6, wherein the relational database includes separate respective tables for users, clinical sites, permissions, eligibility data, randomization data, data on follow-up visits, endpoint status data and significant events data.

8. The computer system of claim 1, wherein the routine for randomization of the subjects to respective treatment strategies includes a randomization module for randomization of the subjects to respective treatment strategies in response to demographic and medical data.

9. The computer system of claim 1, wherein the host computer including means for receiving identification, demographic and medical data about the subjects from the participating sites further includes a relational database with tables and wherein the Internet network server executes a script for transferring data between data communication files transferred on the Internet and the tables of said relational database.

10. A method for managing a clinical study of a treatment strategy to be prescribed for subjects distributed at a plurality of participating sites which are geographically distributed in relation to a study management site, said method comprising:
   inputting identification, demographic and medical data at said participating sites for respective subjects and transmitting said identification, demographic and medical data over the Internet to said study management site;
   receiving said identification, demographic and medical data at an Internet server computer at the study management site;
   transferring said identification, demographic and medical data from said Internet server computer to a host computer;
   executing a randomization routine in the Internet server computer with respect to a subject for which identification, demographic and medical data has been received to assign the subject to a respective treatment strategy, and according to said treatment strategy transmitting a proposed prescription to a respective participating site; and
   receiving and displaying said proposed prescription on a computer at said respective clinical site.

11. The method of claim 10, further comprising the step of adjusting or confirming said proposed prescription under direction of a physician while said proposed prescription is being displayed on the computer at said respective clinical site.

12. The method of claim 11, further comprising the steps of:

transmitting said proposed prescription as determined by said physician from said computer at said respective clinical site over said Internet to said Internet server computer, and eventually to said host computer; and transmitting said physician-determined prescription from said Internet network server computer to a distribution center for filling said drug prescription for the subject.

13. The method of claim 11, further comprising the step of printing out a copy of the prescription for signature by a physician.

14. The method of claim 11, further comprising the step of:

transmitting said proposed prescription as determined by said physician from said computer at said respective clinical site over said Internet to said Internet server computer, and eventually to said host computer; and wherein in said transfer of identification, demographic and medical data to a host computer further comprises inputting said identification, demographic and medical data into a relational database stored in said host computer; and wherein said database is updated with said proposed prescription as determined by said physician.

15. The method of claim 10, wherein said step of transmitting a proposed prescription to a respective participating site provides limits to modifying said prescription according to a range of prescriptions determined for the clinical study.

16. The method of claim 10, further comprising:

inputting follow-up data at said clinical sites for respective subjects and transmitting said follow-up data over the Internet to said study management site;

receiving said follow-up data at an Internet server computer at the study management site;

transferring said follow-up data to a host computer;

executing a control routine in the host computer with respect to a subject for which follow-up data has been received to assign the subject to a stepped or non-stepped treatment strategy, and according to said treatment strategy transmitting a proposed prescription to a respective clinical site; and receiving and displaying said proposed prescription on a computer at said respective clinical site.

17. A method for interactive prescription by a plurality of clinical study investigators at a plurality of geographically distributed sites, said method comprising:

inputting data at one of said distributed sites for a respective subject and transmitting said data over the Internet to a computing center;

receiving said data at said computing center;

executing a routine in a computer at the computing center with respect to said dat a received from said one of the distributed sites to determine a responsive form to be sent to said one of the distributed sites in which further data to be input to the computing center is limited by a parameter determined by said computer in said computing center; and receiving and displaying said f orm at said one of the distributed sites;

inputting further data comprising a prescription into said form at said one of the distributed sites and transmitting said prescription to the computing center; and transmitting said prescription from said computing center to a distribution facility for distributing a prescribed item to a subject in response to the prescription received from said one of the distributed sites.

18. The method of claim 17, wherein the computing center further comprises an Internet server computer and a database host computer having a database therein.

19. The method of claim 18, wherein the database is behind a firewall provided by the Internet server computer, so that the database is inaccessible to computers at the distributed sites.

20. The method of claim 19, further comprising the step of executing a script in the Internet server computer to transfer data between the Internet server computer and the database.

* * * * *